(12) United States Patent
Lessley et al.

(10) Patent No.: US 7,771,786 B2
(45) Date of Patent: Aug. 10, 2010

(54) STRAND ORIENTATION ALIGNMENT IN STRAND COATING SYSTEMS AND METHODS

(75) Inventors: M. Steve Lessley, Villa Hills, KY (US); Rico R. Valentin, Gallatin, TN (US); Edward W. Bolyard, Old Hickory, TN (US)

(73) Assignee: Illinois Tool Works Inc., Glenview, IL (US)

( * ) Notice: Subject to any disclaimer, the term of this patent is extended or adjusted under 35 U.S.C. 154(b) by 676 days.

(21) Appl. No.: 11/079,663

(22) Filed: Mar. 14, 2005

(65) Prior Publication Data

US 2005/0158465 A1 Jul. 21, 2005

Related U.S. Application Data

(62) Division of application No. 10/623,294, filed on Jul. 18, 2003, now Pat. No. 7,485,187.

(51) Int. Cl.
*B05D 5/10* (2006.01)

(52) U.S. Cl. .................. 427/207.1; 427/208.4

(58) Field of Classification Search .................. None
See application file for complete search history.

(56) References Cited

U.S. PATENT DOCUMENTS

| | | | |
|---|---|---|---|
| 2,841,020 A | 7/1958 | Van Deventer | |
| 3,125,126 A | 3/1964 | Engles | |
| 3,667,846 A | 6/1972 | Nater et al. | |
| 3,893,412 A * | 7/1975 | Louch et al. ................ | 118/420 |
| 3,988,086 A | 10/1976 | Marshall et al. | |
| 4,044,250 A | 8/1977 | Fetzer | |
| 4,215,939 A | 8/1980 | Miller et al. | |
| 4,458,152 A | 7/1984 | Bonora | |
| 4,495,126 A | 1/1985 | Deeken et al. | |
| 4,687,477 A | 8/1987 | Suzuki et al. | |
| 4,750,960 A | 6/1988 | Bubeck | |
| 4,842,666 A | 6/1989 | Werenicz | |
| 5,525,175 A | 6/1996 | Blenke et al. | |
| 5,660,664 A | 8/1997 | Herrmann | |
| 5,735,788 A | 4/1998 | Yasutake et al. | |
| 5,766,411 A | 6/1998 | Wilson | |
| 5,964,973 A | 10/1999 | Heath et al. | |
| 6,077,375 A | 6/2000 | Kwok | |
| 6,180,166 B1 * | 1/2001 | Wood et al. .................. | 427/177 |
| 6,520,237 B1 | 2/2003 | Bolyard | |
| 6,582,518 B2 * | 6/2003 | Riney .......................... | 118/325 |
| 6,613,146 B2 | 9/2003 | Bolyard | |
| 2003/0079681 A1 | 5/2003 | Hardy | |
| 2003/0082309 A1 * | 5/2003 | Hayder et al. ................ | 427/421 |

OTHER PUBLICATIONS

ITW Dynatec, Integra System, http:///www.itwdynatec.com/integra.htm.
Nordson Corp., "Non-Woven Systems" (9) website pages, 1998.

* cited by examiner

*Primary Examiner*—Frederick J Parker
(74) *Attorney, Agent, or Firm*—Law Offices of Steven W. Weinrieb

(57) ABSTRACT

A strand coating system and method including drawing (710) a strand having major and minor dimensions past an adhesive dispensing nozzle, orienting (720) at least a portion of the strand so that the major dimension of the strand is substantially parallel to a direction in which adhesive is dispensed from the adhesive dispensing nozzle as the portion of the strand is drawn past the adhesive dispensing nozzle, and applying (730) adhesive to the strand as the strand is drawn past the adhesive dispensing nozzle.

17 Claims, 5 Drawing Sheets

STRAND ORIENTATION ALIGNMENT IN STRAND COATING SYSTEMS AND METHODS

CROSS REFERENCE TO RELATED APPLICATION

The present application is a division of commonly assigned, U.S. application Ser. No. 10/623,294 filed on 18 Jul. 2003 now U.S. Pat. No. 7,485,187 entitled "Strand Orientation Alignment In Strand Coating System And Methods", which is incorporated by reference herein.

FIELD OF THE DISCLOSURE

The present disclosure relates generally to strand coating systems and methods, and more particularly to systems, subsystems and methods for applying coatings to elongated strands having asymmetric cross sections, for example, the application of vacillating adhesive filaments to elastic strands having rectangular cross sections prior to adherence on a substrate or between substrates, methods and systems therefor.

BACKGROUND

It is known generally to apply adhesive coatings to elongated strands. U.S. Pat. No. 6,077,375 entitled "Elastic Strand Coating Process", for example, discloses the application of vacillating adhesive filaments dispensed from a nozzle onto elastic and other strands, some of which are adhered onto a substrate or in some applications between adjacent substrates. In one exemplary application disclosed in U.S. Pat. No. 6,077,375, a vacillating meltblown adhesive filament is captured on an elastic strand drawn past a nozzle from which the adhesive is dispensed. And in some applications in U.S. Pat. No. 6,077,375, the vacillating adhesive filament is substantially entirely captured by the strand as it tends to wrap around the strand, coating the sides thereof substantially uniformly along the strand axis prior to adherence of the strand onto a substrate in the manufacture of bodily fluid absorbing personal hygienic articles.

It is also known to align elongated strands with a nozzle from which an adhesive filament is dispensed by drawing the strands over a grooved guide roller located upstream of the nozzle, as disclosed, for example, the referenced U.S. application Ser. No. 09/758,702 entitled "Variable Spacing Strand Coating System And Modular Guide Roller Therefor" and the referenced U.S. application Ser. No. 09/621,721 entitled "Variable Spacing Strand Coating System And Method". See also, the ITW DYNATEC INTEGRA strand coating system.

The known exemplary strand coating systems and technologies discussed above work well for applying adhesive materials to elastic strands having substantially uniform cross-sections, for example, square or circular cross-sectional shapes. In some applications, however, the adhesive or other substance is applied to a strand having an asymmetric cross sectional shape, for example, a substantially rectangular sectional shape. These applications include the application of adhesives onto natural rubber or elastic tape used in the manufacture of bodily fluid absorbent hygienic articles. In applications where the cross-sectional shape of the elastic strand is rectangular or asymmetric, the known prior art adhesive coating systems tend to apply the adhesive material on the elastic strand unevenly. Specifically, the adhesive tends to adhere more on one side of the strand, for example, the wider edge thereof, than to other sides of the strand. Moreover, in some applications, the strand tends to flip from side to side as it is drawn along the strand guide resulting in the application of the adhesive material to different sides of the strand. In some applications, for example, those where the strand is bonded between substrates, among others, the uneven application of adhesive material to the strand compromises the integrity of the bond, since some portions of the strand may be devoid of adhesive.

The objects, aspects, features and advantages of the present disclosure will become more fully apparent upon careful consideration of the following Detailed Description thereof and the accompanying Drawings, which may be disproportionate for ease of understanding, wherein like structure and steps are referenced generally by corresponding numerals and indicators.

DETAILED DESCRIPTION

The disclosure is drawn generally to systems, sub-systems and methods for controlling the orientation of at least a portion of a strand about its axial dimension as the strand portion is drawn past a fluid or liquid dispensing nozzle, for example, in an adhesive dispensing system that applies a hot melt adhesive filament from an adhesive dispensing orifice of an adhesive dispensing device or apparatus onto an elastic strand used in the manufacture of personal hygienic articles. According to the disclosure, these and other adhesive dispensing systems generally include a strand axial orientation aligning member.

Figure 2:
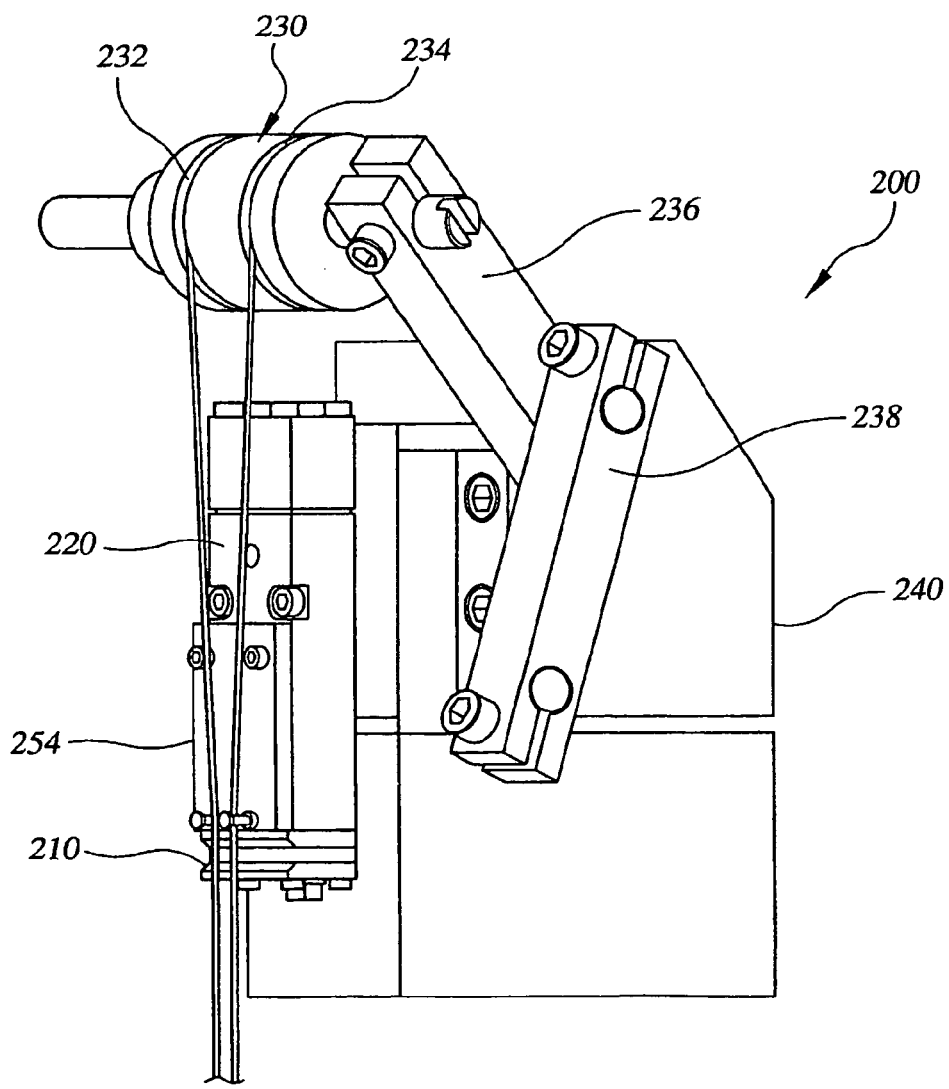
FIG. 2 is a first view of an exemplary strand coating system.
Figure 3:
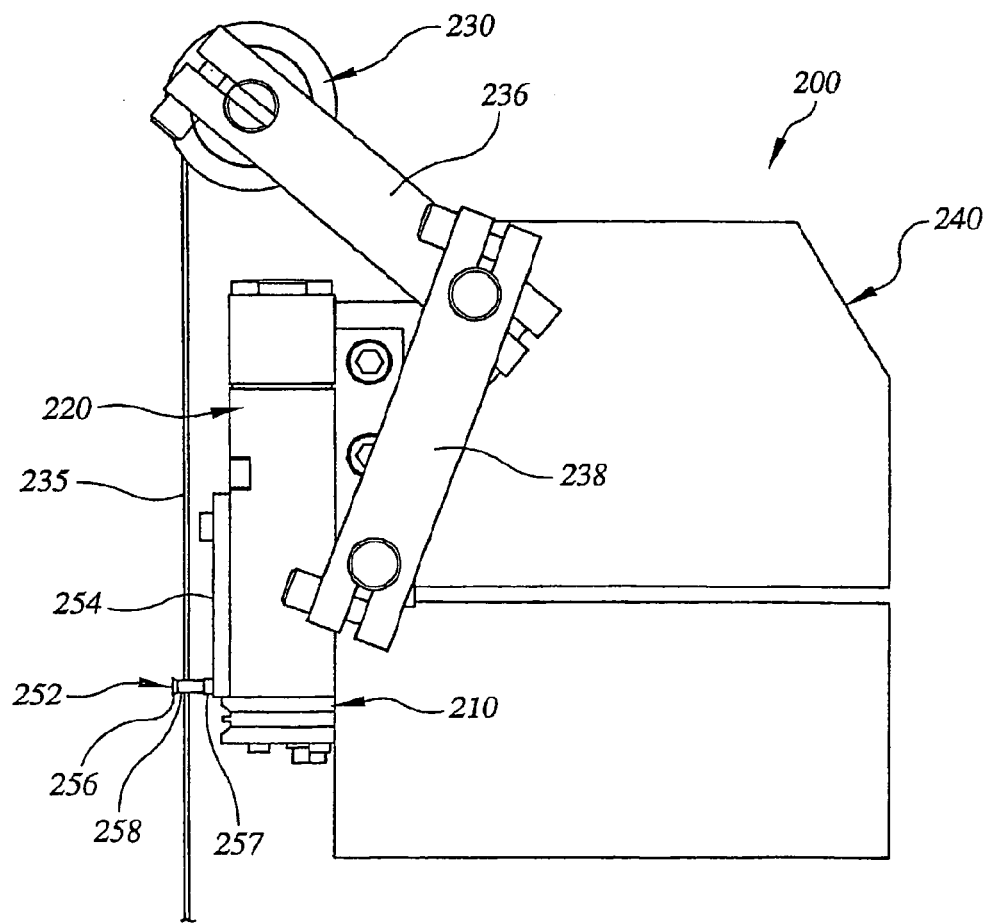
FIG. 3 is a second view of the exemplary strand coating system.
Figure 4:
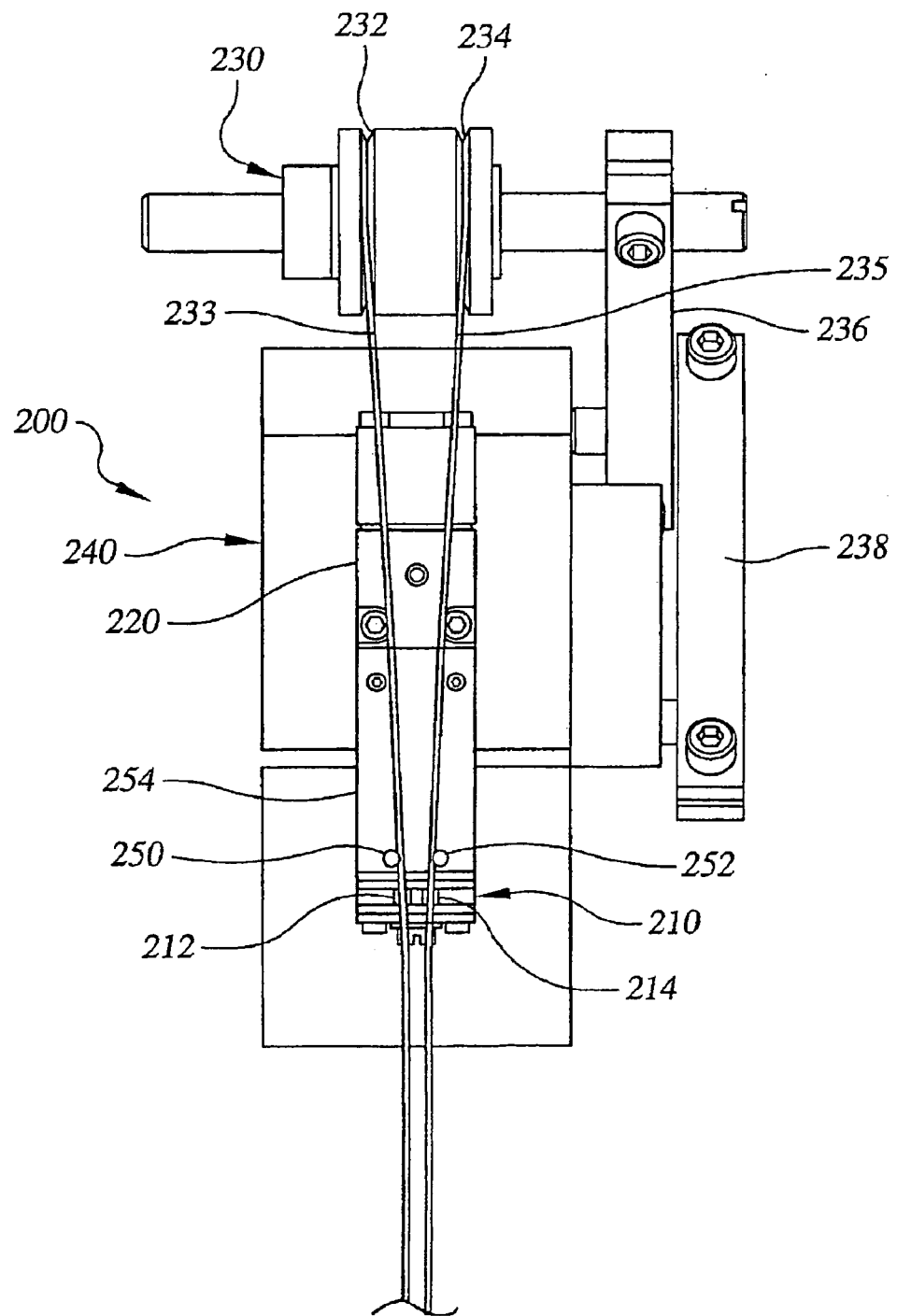
FIG. 4 is a third view of the exemplary strand coating system.

FIGS. 2-4 illustrate an exemplary strand coating system 200 including generally an adhesive dispensing device 210 having one or more adhesive dispensing orifices. In the exemplary embodiment of FIG. 4, the adhesive dispensing device 210 includes first and second orifices 211 and 212 that each dispense an adhesive fiber or filament onto a corresponding strand. In one exemplary strand coating application, the adhesive filaments vacillate predominately transversely to the path of the corresponding strands. These and related filament producing apparatuses are known generally and discussed more fully, for example, in U.S. Pat. No. 6,200,635 entitled "Omega Spray Pattern And Method", in U.S. Pat. No. 5,902,540 entitled "Meltblowing Method And Apparatus" and in U.S. Pat. No. 5,902,298 entitled "Improved Meltblowing System", among other references in the prior art. However, the disclosure is not limited to any particular type of fluid or liquid dispensing apparatus or system.

In alternative embodiment, the adhesive dispensing system or device is a spiral nozzle that dispenses a generally helical filament or fiber. In other embodiments, other filament dispensing devices may be used alternatively. Although the exemplary applications concern the application of adhesive fibers or filaments onto elastic strands, the disclosure has much wider applicability, including the application filaments onto other strand types, which are not necessarily elastic, and to the application of atomized liquids onto strands, for example, the application of atomized lubricants onto fibers, among other applications, as will be appreciated in view of the discussion below.

In the FIGS. 2-4, the exemplary adhesive dispensing device 210 is mounted on a module 220 that controls the supply of adhesive and air or other gas to the adhesive dispensing device 210. The module may be operated pneumatically or electrically. The module 220 or similar device may also be used to control the supply of adhesive and/or air to spiral nozzles and to other adhesive dispensing devices, for example, to spiral nozzles. The exemplary module 220 is mounted on a head 240, which provides a metered supply of adhesive or other material and air to the adhesive dispensing device via the module. In other embodiments, the adhesive and any required gas may be provided to the nozzle by some other structure, for example, the adhesive dispensing orifices may be part of an integrated assembly rather than the modular assembly of the exemplary embodiment.

The exemplary system of FIGS. 2-4 also includes an optional strand guide member 230 for guiding and aligning the strand along a drawing path relative to the adhesive dispensing nozzle. In FIGS. 2 and 4, the exemplary strand guide 230 is a strand guide roller having first and second grooves 232 and 234 for guiding corresponding strands 233 and 235 relative to corresponding orifices of the adhesive dispensing device 210. In other embodiments, other types of strand guides may be used, for example, non-rotating strand guides. The strand guide is generally located upstream of the adhesive dispensing device and functions generally to align the path of one more strands with the adhesive dispensing device. In some embodiments, the strand guide is not required.

In embodiments where a strand guide is employed and in applications subject to vibration, the strand guide is preferably coupled to the adhesive dispensing device so that the strand guide and adhesive dispensing device vibrate in unison. In the exemplary embodiment of FIGS. 2-4, the stand guide roller 230 is adjustably mounted on the head 240 by first and second adjustably positionable arms 236 and 238, which permit adjusting the spacing between the strands and the adhesive dispensing device and also permit adjusting the upstream location of the strand guide roller. In other embodiments, the strand guide roller is not necessarily coupled to the adhesive dispensing device, and the strand guide position is not necessarily adjustable.

According to another aspect of the disclosure, at least one strand axial orientation aligning member is disposed proximate each orifice of the fluid or liquid dispensing device. In applications where an adhesive or other material is applied to the strand, the strand axial orientation aligning member is preferably disposed on an upstream side of adhesive dispensing device. In the exemplary embodiment of FIGS. 2-4, a strand axial orientation aligning member 252 is positioned between each orifice of the fluid or liquid dispensing device and the strand guide roller 230. In one embodiment, the strand axial orientation aligning member is positioned so that it is generally aligned with a corresponding orifice, for example, on one side or the other thereof, of the adhesive dispensing device. Generally, the strand is drawn so that it passes along the strand axial orientation aligning member and over or under a corresponding orifice of the fluid or liquid dispensing device.

Figure 8:
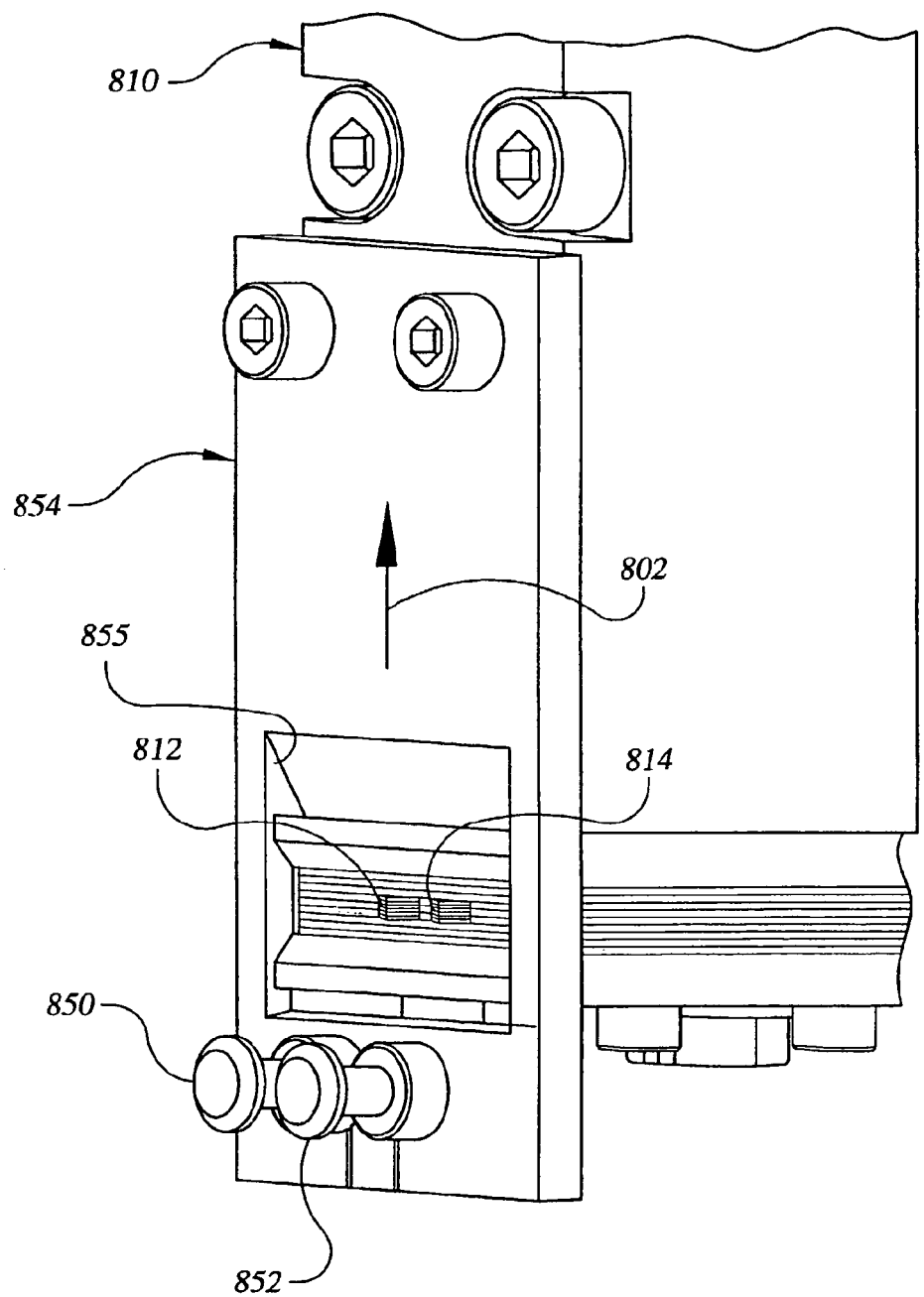
FIG. 8 is an exemplary strand axial orientation aligning member mounting bracket.

In the exemplary embodiment of FIG. 4, first and second strand axial orientation aligning members 250 and 252 are aligned generally with corresponding orifices 212 and 214, respectively, of the adhesive dispensing device 210. In FIGS. 2-4, the exemplary strand axial orientation aligning members are mounted on a plate 254 fastened to the module 220. The exemplary strand axial orientation aligning member is a pin shaped member having an axis extending substantially transversely to a direction in which the strand is drawn past the adhesive dispensing device. In the alternative embodiment of FIG. 8, an alternative mounting plate 854 is configured so that first and second strand axial orientation aligning members 850 and 852 are aligned generally with corresponding orifices 812 and 814, respectively, of the adhesive dispensing device 810 on an opposite side of the orifices 812 and 814. The alternative mounting plate of FIG. 8 is suitable for applications where the strand is drawn in the direction of arrow 802, thus positioning the strand axial orientation aligning members on an upstream side of the orifices. The mounting plate 854 of FIG. 8 is distinguished from the mounting plate 254 of FIG. 2 by an opening 855 that permits the orifices to dispense material without obstruction. In other embodiments, however, the strand axial orientation aligning members are not mounted or otherwise coupled to the adhesive dispensing device. For example, the strand axial orientation aligning members may be mounted or supported by some other isolated structure.

Generally, the strand axial orientation aligning member controls an orientation of at least a portion of the strand about its axial dimension as the strand portion is drawn past the adhesive dispensing nozzle. The strand axial orientation aligning member also precisely aligns the strand with the orifice of the adhesive dispensing device. In the exemplary strand coating application, the strand axial orientation aligning member controls the orientation of the strand portion by preventing twisting of the strand portion about its axial dimension at least in a neighborhood of the adhesive dispensing nozzle. Thus the strand axial orientation aligning member fixes the orientation of the strand at least as the strand is drawn past the orifice of the adhesive dispensing nozzle.

In FIG. 3, the exemplary strand axial orientation aligning member includes first and second flanges 256 and 257 separated by a guiding portion 258. The strand 235 is retained between the first and second flanges, thereby essentially fixing the distance between the strand and the adhesive dispensing device 210. Structure other than the strand axial orientation aligning member may be used alternatively to fix the distance between the strand and the device in embodiments where it is desirable to control or fix the spacing between the strand and the orifice.

Figure 5:
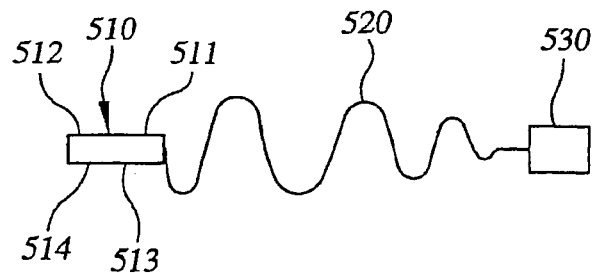
FIG. 5 illustrates a strand oriented relative to an fluid dispensing nozzle.

In one embodiment, the strand has at least one relatively flat side or surface along its axial dimension. In FIG. 5, for example, the exemplary strand 510 has a substantially rectangular cross-sectional shape with major and minor axes or dimensions. The major dimension has flat sides 511 and 513 along the axial direction of the strand. The orientation of the strand portion about its axial dimension is controlled by engaging the substantially flat side of the strand with the strand axial orientation aligning member as the strand is drawn past the fluid or liquid dispensing device. In FIG. 5, the strand is oriented so that the major axis of the cross-sectional dimension of the strand is substantially parallel to the direction in which a vacillating adhesive filament 520 is dispensed from a dispensing device 530 by a similarly aligned strand axial orientation aligning member, which is not visible in FIG. 5. The strand orientation illustrated in FIG. 5 is desirable in some strand coating applications, for example, those where the strand is coated with a vacillating filament or fiber as illustrated in FIG. 5 to ensure that the strand is coated on both sides 512 and 514 along its major dimension or axis. In other embodiments, the strand may be oriented at different angles by orienting the angle of the guiding surface of the strand axial orientation aligning member. For example, the major dimension of the strand cross-section may be made substantially transverse to the direction of the adhesive flow with a transversely disposed strand axial orientation aligning member. In other embodiment, the strand may be oriented at other angles.

Figure 1:
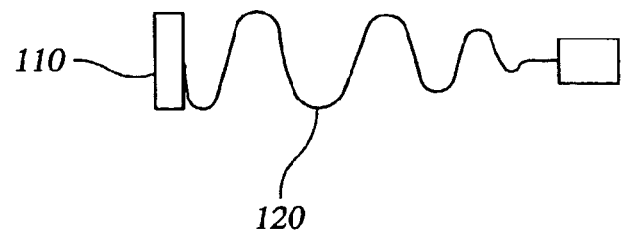
FIG. 1 illustrates an adhesive material applied to one side of an exemplary strand having a substantially rectangular cross-sectional shape.

In FIG. 1, where the major dimension of the rectangular strand 110 is aligned transversely to the path of the filament 120, the strand tends to be coated on only one side thereof. The filament in FIG. 1 may be a substantially planar vacillating filament or a helical filament. Also, in many stand coating applications, the strand tends to twist back and forth about its axial dimension as it is drawn past the adhesive dispensing device, for example, in applications where the strand is subject to vibration. If the twisting strand is symmetrical about its axial dimension the twisting thereof may not have an adverse affect on the application of adhesive onto the strand. However, in applications where the twisting strand has a rectangular cross-section, the twisting strand tends to be coated on only one side thereof facing the orifice when the major dimension of the strand is transverse to the path of the adhesive filament. Thus a twisting strand having a rectangular cross-sectional dimension will not be uniformly coated with adhesive along its axial dimension.

Figure 6:
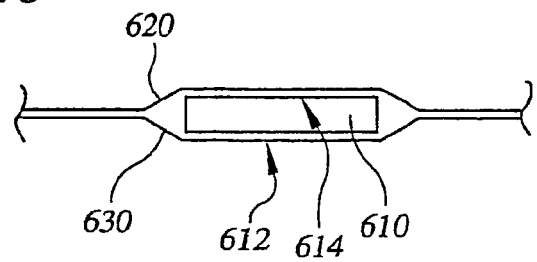
FIG. 6 illustrates an exemplary strand having a substantially rectangular cross-sectional shape disposed between substrates.

While not an issue for some applications, partial or incomplete applications of adhesive along the axial dimension of the strand is problematic for others. FIG. 6 illustrates an application where an adhesive coated strand 610 is bonded between first and second substrates 620 and 630, for example, in the manufacture of personal hygienic articles. Thus in applications like those illustrated in FIG. 6, it is desirable to uniformly coat the strand on both sides 612 and 614 along its major axis to ensure complete bonding along the axial dimension of the strand. Orienting the strand as illustrated in FIG. 5, with a strand axial orientation aligning member will ensure uniform coating of the strand on opposite sides of the major dimension along the axial dimension of the strand.

In the exemplary embodiment, a tangential force is applied to the strand as the strand is drawn over the strand axial orientation aligning member by guiding the strand in a groove of the strand guide roller that is not aligned with the adhesive dispensing orifice, as illustrated best in FIG. 4. Particularly, one of the grooves 232 or 234 of the strand guide roller guide the strand along a path that is misaligned with the orifices 212 and 214 of the adhesive dispensing device. A corresponding one of the strand axial orientation aligning members 250 or 252 change the direction of the strand 233 and 235 in alignment with the orifices 212 and 214. The tangential force biases the strand against the strand axial orientation aligning member as the strand is drawn past the adhesive dispensing device. The biasing force enables the strand axial orientation aligning member to maintain the desired orientation of the strand about its axial dimension at least in a neighborhood of the adhesive dispensing device. In an alternative embodiment, not illustrated, the strand may be captured between two strand axial orientation aligning members. In the alternative embodiment, it may by unnecessary to tangentially bias the strand about the strand axial orientation aligning member with a misaligned strand guide.

Figure 7:
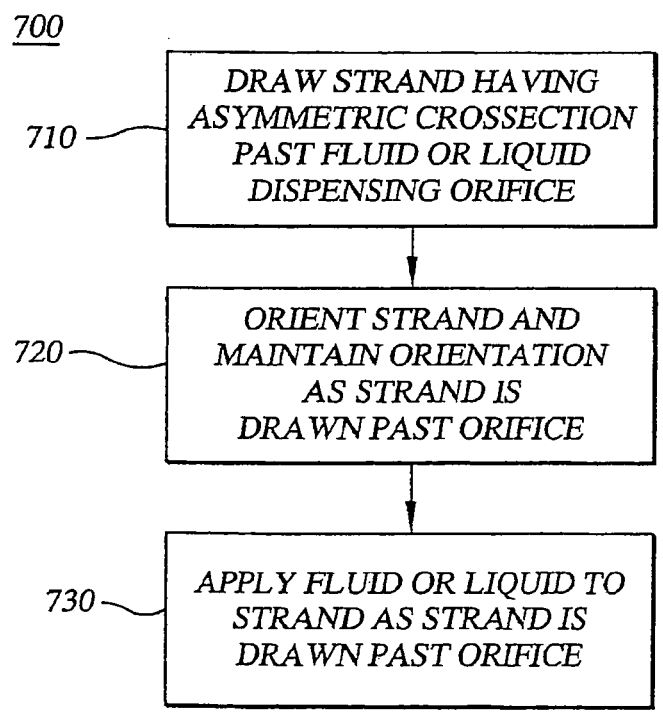
FIG. 7 is an exemplary process diagram.

In the exemplary strand coating process diagram 700 of FIG. 7, at block 710, a strand having an asymmetric cross-sectional shape, for example, a rectangular shape with major and minor dimensions, is drawn past an adhesive dispensing nozzle. In some embodiments, the strand is aligned along a drawing path relative to the adhesive dispensing nozzle before orienting the portion of the strand, for example, with a strand guide roller.

At block 720, an orientation of at least a portion of the strand is maintained as the portion of the strand is drawn past the adhesive dispensing nozzle. In the exemplary adhesive dispensing application, the major dimension of the strand is aligned and fixed substantially parallel to a direction in which adhesive is dispensed from the adhesive dispensing nozzle. In some applications, orientation includes preventing twisting of the portion of the strand oriented to maintain its orientation relative to the adhesive dispensing nozzle as the portion of the strand is drawn past the adhesive dispensing nozzle.

In FIG. 7, at block 730, a liquid or fluid, for example, a hot melt adhesive is applied to the strand as the strand is drawn past the adhesive dispensing nozzle. In some embodiments, applying adhesive to the strand as the strand is drawn past the adhesive dispensing nozzle includes capturing a vacillating filament dispensed from the adhesive dispensing nozzle on opposite sides of the strand substantially parallel to the direction in which adhesive is dispensed from the adhesive dispensing nozzle. In other embodiments, however, the adhesive filament may not be vacillating, for example, it may be a spiral filament or a filament exhibiting chaotic behavior. Also, in some embodiments, it may not be desirable to capture the filament on both sides of the strand. For example, in some applications, it is desirable capture the filament on only one side of the strand, by having its major dimension oriented transversely to the general direction of the filament.

While the foregoing written description of the disclosure enables one of ordinary skill to make and use what are considered presently to be the best modes thereof and evidences the rightful possession thereof, those of ordinary skill will understand and appreciate the existence of variations, combinations, and equivalents of the specific exemplary embodiments herein. The inventions are therefore to be limited not by the exemplary embodiments herein, but by all embodiments within the scope and spirit of the appended claims.

What is claimed is:

1. A method in a strand coating system, the method comprising:
   drawing a strand having major and minor dimensions past an adhesive dispensing nozzle,
   orienting at least a portion of the strand so that the major dimension of the strand is substantially parallel to a direction in which adhesive is dispensed from the adhesive dispensing nozzle as the portion of the strand is drawn past the adhesive dispensing nozzle;
   preventing twisting of the portion of the strand oriented so that the major dimension of the strand is substantially parallel to a direction in which adhesive is dispensed from the adhesive dispensing nozzle as the portion of the strand is drawn past the adhesive dispensing nozzle;
   applying adhesive to the strand as the strand is drawn past the adhesive dispensing nozzle.

2. The method of claim 1, applying adhesive to the strand as the strand is drawn past the adhesive dispensing nozzle includes capturing a vacillating adhesive filament dispensed from the adhesive dispensing nozzle on opposite sides of the strand oriented substantially parallel to the direction in which adhesive is dispensed from the adhesive dispensing nozzle.

3. The method of claim 1, aligning the strand along a drawing path relative to the adhesive dispensing nozzle before orienting the portion of the strand.

4. The method of claim 1,
   guiding the strand along a first path with a first strand guiding member, the first path not aligned with the adhesive dispensing nozzle,
   guiding the strand along a second path with a second strand guiding member, the second path aligned with the adhesive dispensing nozzle,
   the second strand guiding member located between the first strand guiding member and the adhesive dispensing nozzle,
   orientating the strand about its axial dimension so that the major dimension of the strand is substantially parallel to the direction in which adhesive is dispensed from the adhesive dispensing nozzle with the second strand guiding member, the axial dimension of the strand substantially parallel to a direction in which the strand is drawn.

5. The method of claim 1, guiding the strand with a first strand guide member, orientating the strand about its axial dimension so that the major dimension of the strand is substantially parallel to the direction in which adhesive is dispensed from the adhesive dispensing nozzle with a second strand guiding member.

6. The method of claim 1, maintaining a spacing between the strand and the adhesive dispensing nozzle, maintaining the spacing and orientation of the strand by drawing the strand along a recess disposed in a pin extending substantially parallel a direction of the adhesive dispensing nozzle.

7. A method in a system for applying coating materials onto a strand, the system including a fluid dispensing device having a fluid dispensing orifice from which fluid is dispensed, the method comprising:

drawing a strand past the fluid dispensing orifice of the fluid dispensing device, the drawn strand spaced apart from the fluid dispensing orifice in a region where fluid is dispensed from the fluid dispensing orifice;

orienting at least a portion of the strand about an axial dimension of the strand as the portion of the strand is drawn past the fluid dispensing orifice, the axial dimension of the strand substantially parallel to a direction in which the strand is drawn, orienting the strand about its axial dimension by engaging the strand with a strand orienting pin having an axial dimension extending substantially parallel to a direction in which fluid is dispensed from the fluid dispensing orifice.

8. The method of claim 7, orienting the strand about its axial dimension by engaging the strand with the strand orienting pin extending substantially transversely to direction in which the strand is drawn.

9. The method of claim 8, maintaining a spacing between the strand and the fluid dispensing nozzle by guiding the strand in a recess on the strand orienting pin.

10. The method of claim 8, guiding the strand with a strand guide, the strand orienting pin located between the strand guide and the fluid dispensing device.

11. The method of claim 8, orienting the strand about its axial dimension includes preventing twisting of the strand portion as the strand portion is drawn past the fluid dispensing orifice of the fluid dispensing device.

12. The method of claim 8, the system is an adhesive dispensing system, dispensing adhesive onto, the oriented strand portion as the strand portion is drawn past the fluid dispensing orifice.

13. A method in a strand coating system, the method comprising:

drawing a strand past an adhesive dispensing nozzle, the strand having an axial dimension substantially transverse to a cross-section of the strand;

guiding the strand along a first path with a first strand guiding member, the first path not aligned with the adhesive dispensing nozzle, guiding the strand along a second path with a second strand guiding member, the second path aligned with the adhesive dispensing nozzle, the second strand guiding member located between the first strand guiding member and the adhesive dispensing nozzle;

controlling an orientation of at least a portion of the strand with the second strand guiding member as the portion of the strand is drawn past the adhesive dispensing nozzle, controlling the orientation of the portion of the strand includes preventing twisting of the portion of the strand about its axial dimension as the portion of the strand is drawn past the adhesive dispensing nozzle.

14. The method of claim 13, aligning the strand along a drawing path relative to the adhesive dispensing nozzle with a strand guide member.

15. The method of claim 13, guiding the strand with a first strand guiding member, controlling the orientation of the strand about its axial dimension with a second strand guiding member located between the first strand guiding member and the adhesive dispensing nozzle.

16. A method in a strand coating system, the method comprising:

drawing a strand past an adhesive dispensing nozzle, the strand having an axial dimension substantially transverse to a cross-section of the strand and the strand having at least one substantially flat side along its axial dimension;

controlling an orientation of at least a portion of the strand about its axial dimension as the portion of the strand is drawn past the adhesive dispensing nozzle, controlling the orientation of the portion of the strand includes preventing twisting of the portion of the strand about its axial dimension as the portion of the strand is drawn past the adhesive dispensing nozzle;

controlling the orientation of the portion of the strand about its axial dimension by engaging the substantially flat side of the strand with a pin extending substantially transverse to a direction in which the strand is drawn.

17. A method in a strand coating system, the method comprising:

drawing a strand past an adhesive dispensing nozzle, the strand having an axial dimension substantially transverse to a cross-section of the strand and the strand having a substantially rectangular cross-sectional shape with minor and major dimensions;

controlling an orientation of at least a portion of the strand about its axial dimension as the portion of the strand is drawn past the adhesive dispensing nozzle, controlling the orientation of the portion of the strand includes preventing twisting of the portion of the strand about its axial dimension as the portion of the strand is drawn past the adhesive dispensing nozzle;

controlling the orientation of the strand includes aligning the major dimension of the strand substantially parallel with a direction in which the adhesive dispensing nozzle dispenses adhesive.

* * * * *